(12) United States Patent
Etzdorf

(10) Patent No.: US 10,994,066 B2
(45) Date of Patent: May 4, 2021

(54) INFUSION LINE WITH A FACILITY TO PROMOTE MIXING OF AN INFUSION SOLUTION WITH A FURTHER FLUID, APPARATUSES AND METHOD

(71) Applicant: Fresenius Medical Care Deutschland GmbH, Bad Homburg (DE)

(72) Inventor: Dirk Etzdorf, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 606 days.

(21) Appl. No.: 15/535,483

(22) PCT Filed: Dec. 21, 2015

(86) PCT No.: PCT/EP2015/080815
§ 371 (c)(1),
(2) Date: Jun. 13, 2017

(87) PCT Pub. No.: WO2016/102479
PCT Pub. Date: Jun. 30, 2016

(65) Prior Publication Data
US 2017/0340796 A1    Nov. 30, 2017

(30) Foreign Application Priority Data
Dec. 22, 2014 (DE) .......................... 102014119445.4

(51) Int. Cl.
*A61M 1/34* (2006.01)
*A61M 1/36* (2006.01)
*A61M 5/142* (2006.01)

(52) U.S. Cl.
CPC ........ *A61M 1/3434* (2014.02); *A61M 1/3437* (2014.02); *A61M 1/367* (2013.01);
(Continued)

(58) Field of Classification Search
CPC .. A61M 1/3675; A61M 1/3434; A61M 1/367; A61M 2205/3337; A61M 2206/10;
(Continued)

(56) References Cited

U.S. PATENT DOCUMENTS 3,511,238 A    5/1970 Wrangell
4,411,652 A *  10/1983 Kramer ............. A61M 5/14224
                                                    417/478

(Continued)

FOREIGN PATENT DOCUMENTS

DE        42 40 681        6/1994
DE        4240681 A1 *     6/1994 .......... A61M 1/3465
(Continued)

OTHER PUBLICATIONS

English translation of International Search Report issued in PCT/EP2015/080815 dated Mar. 18, 2016, 10 pages.
(Continued)

*Primary Examiner* — Leslie R Deak
(74) *Attorney, Agent, or Firm* — Fish & Richardson P.C.

(57) ABSTRACT

The present disclosure relates to an addition line for adding an infusion solution to a fluid, which flows in an extracorporeal blood circuit, wherein the addition line comprises a pressure release valve or a check valve. It further relates to an extracorporeal blood circuit, a blood treatment apparatus and a method using the addition line.

10 Claims, 2 Drawing Sheets

(52) U.S. Cl.
CPC .......... *A61M 1/3675* (2013.01); *A61M 5/142* (2013.01); *A61M 2205/3337* (2013.01); *A61M 2206/10* (2013.01)

(58) Field of Classification Search
CPC ... A61M 5/142; A61M 1/3424; A61M 1/1602
See application file for complete search history.

(56) References Cited

U.S. PATENT DOCUMENTS

| | | | |
|---|---|---|---|
| 2005/0131331 A1* | 6/2005 | Kelly | A61M 1/3434 604/4.01 |
| 2008/0154170 A1 | 6/2008 | Lannoy | |
| 2013/0028788 A1 | 1/2013 | Gronau et al. | |

FOREIGN PATENT DOCUMENTS

| | | |
|---|---|---|
| DE | 102010047747 | 4/2012 |
| EP | 0 165 519 | 12/1985 |
| EP | 1 666 078 | 6/2006 |
| EP | 2183004 | 5/2010 |
| WO | WO 2007/101064 | 9/2007 |
| WO | WO 2009/030973 | 3/2009 |
| WO | WO 2015/000934 | 3/2009 |
| WO | WO 2014/026771 | 2/2014 |

OTHER PUBLICATIONS

Association for the Advancement of Medical Instrumentation, "Cardiovascular Implants and Artificial Organs—Extracorporeal Blood Circuit for Haemodialyzers, Haemodiafilters and Haemofilters," ANSI/AAMI, 2007, RD17:2-3, 150-151.

Shaldon et al., "Haemodialysis Monitors and Monitoring," Replacement of Renal Function by Dialysis, Drukker et al. (ed), 1978, 260-261.

English Translation of International Preliminary Report on Patentability in Application No. PCT/EP2015/080815, dated Jun. 27, 2017, 8 pages.

* cited by examiner

INFUSION LINE WITH A FACILITY TO PROMOTE MIXING OF AN INFUSION SOLUTION WITH A FURTHER FLUID, APPARATUSES AND METHOD

CROSS-REFERENCE TO RELATED APPLICATIONS

This application is a U.S. national stage application under 35 USC § 371 of International Application No. PCT/EP2015/080815, filed on Dec. 21, 2015, which claims priority to German Patent Application No. 102014119445.4 filed on Dec. 22, 2014, the entire contents of which are incorporated herein by reference.

TECHNICAL FIELD

The present disclosure relates to an addition line, an extracorporeal blood circuit, a blood treatment apparatus and a method for controlling an infusion pump.

BACKGROUND

Infusion solutions or medicaments are mostly infused through the extracorporeal blood circuit, i.e. the blood tubing system being used for the extracorporeal blood treatment. Depending on the type of the infusion solution, a fast mixing of the infusion solution with the blood may be favorable or desirable.

Anticoagulation infusion solutions are thus infused as standard in an extracorporeal blood treatment to prevent a possible occlusion of the extracorporeal blood circuit.

Two methods are mainly used for this purpose; the systematic and the regional anticoagulation. A citrate solution, which complexes calcium, and thus suppresses the blood coagulation, is mostly used as an anticoagulant in the regional anticoagulation. Prior to returning blood to the patient, an additional calcium is typically administered, since too-low of calcium concentrations influence nerves and muscles, the blood coagulation and functions of lung, heart and kidneys. In the regional anticoagulation, a calcium-containing solution, by which the physiological calcium concentration in the systematic blood and its dotting ability may be restored, is therefore added to the blood before reinfusing it into the patient.

Infusing infusion solutions or medicaments into the tubing system of the extracorporeal blood circuit usually takes place at addition sites with a T-form, the so-called Tees. Laminar flow conditions predominate in these Tees due to the circular cross-section and the smooth inner wall of the addition site. In addition, the flow rates of the infused solution are low in comparison with the blood flow.

The largely laminar flow conditions and the low flow rates of the infusion solutions or medicaments flowing into the blood stream may cause a delayed or only slow mixing of the blood with the added infusion. This slow mixing of both fluids at the addition site is undesired, especially when adding the calcium solution to blood, and may lead to downstream clot formation, due to the punctual high calcium concentrations in blood.

To prevent that, a fast and homogenous mixing of the added calcium solution with the blood is favorable.

This problem may, however also occur when mixing other fluids, e.g. medicaments, where a fast mixing may as well be advantageous.

SUMMARY

An insert piece for a blood tubing system having a spiral structure is described in WO 2014/026771 A1. The spiral structure serves for generating turbulences in the area of the infusion site. The turbulences shall serve for a better mixing.

Some embodiments described herein propose a further aspect for promoting mixing of an infusion solution with a further fluid, e.g. blood.

Therefore, an addition line, which is intended for adding an infusion solution to a fluid flowing in an extracorporeal blood circuit, is proposed. The addition line is therefore intended to be connected to an extracorporeal blood circuit. It is optionally already designed accordingly, for example, with respective connectors, tees or the like.

The addition line comprises at least one pressure release valve.

The extracorporeal blood circuit comprises at least one blood withdrawal line and one addition line.

The blood treatment apparatus is connected to an extracorporeal blood circuit. The latter comprises, as stated supra, at least one addition line and one blood withdrawal line. The blood treatment apparatus further comprises an infusion pump for infusing an infusion solution within or through the addition line, or it is physically or in signal transmission connected to such an infusion pump. It further comprises a blood pump for conveying blood within or through the blood return line. The infusion pump is controlled or regulated by a provided control or regulating device (in short: control device).

The method serves for controlling an infusion pump for conveying an infusion solution within an addition line. It encompasses at least providing an addition line, connecting the infusion pump to a source for the infusion solution, connecting or bringing the infusion pump in contact with a pump section of the addition line and conveying the infusion solution by a preferably continuously or constantly operating of the infusion pump with a continuous flow rate.

Some embodiments may encompass one or more of the previous or following features in any combination and are further subject-matter of the dependent claims.

Whenever a numerical value is mentioned herein, the person skilled in the art understands it as an indication of a numerical lower limit. Unless it leads the person skilled in the art to an evident contradiction, the skilled person implicitly understands when specifying for example "one" always as "at least one". This understanding is also evenhandedly encompassed by certain aspects as the interpretation that a numeric word, for example, "one" may alternatively mean "exactly one", wherever this is not evidently technically impossible for the skilled person. Both are encompassed and apply herein to all used numerical values.

Spatial indications made herein such as "top", "bottom", etc. refer in case of doubt to the illustrations as seen in the accompanying figures.

The pressure release valve may be a check valve.

In certain exemplary embodiments, the pressure release valve is arranged in a section of the addition line. Said section is arranged between a pump section of the addition line, wherein said pump section is provided and/or designed in an infusion pump or may be connected thereto, and a connecting section provided and/or designed to be in fluid communication with a blood line of an extracorporeal blood circuit.

In certain exemplary embodiments, the addition line comprises, or is in fluid communication with, a source for the infusion solution.

The infusion solution may be a calcium solution.

In certain exemplary embodiments, the control device is adapted or programmed to control the infusion pump in order to convey exclusively continuously.

In certain exemplary embodiments, the addition line is in fluid communication with the blood withdrawal line.

In certain exemplary embodiments, the control device is explicitly not adapted or programmed to have the infusion pump convey in a pulsating manner.

Conveying in a pulsating manner, or a thereby-resulting pulsating flow or flow profile, which is a desired or an aimed result of controlling, being achieved by respective control signals is, in some exemplary embodiments, explicitly not a subject-matter or part of the present invention.

With a pulsating flow profile, phases in which the fluid or the infusion solution is conveyed via the infusion pump (flow pulse or pulse) and phases, in which no, or clearly less, fluid is conveyed, may interchange periodically. This leads to a so-called pulsating flow profile. In other words, the infusion pump runs discontinuously, i.e., there are incisive changes in the flow rate of the infusion pump. The infusion pump does not necessarily need to be periodically or regularly stopped in order to generate such a pulsating flow profile. Such controlling is not subject-matter of the present invention.

A pulsating profile may comprise a rectangular profile, a sinusoidal profile, a needle-shaped profile or the like.

In an embodiment of the method, the control device may control or regulate the infusion pump such that it runs continuously to convey the infusion solution with a constant flow.

A continuous conveyance may be understood as a non-pulsating conveyance.

It is self-evident for one skilled in the art, that due to the structure of the infusion pump, e.g. an occluding infusion pump, pressure and flow pulses may emerge. A flow profile technically resulting from the pump structure but not from the control device is not considered in certain exemplary embodiments as a pulsating flow profile and may therefore take place. A pulsating flow profile generated, on the other hand, by the control device, as explained above, is in contrast thereto not encompassed by the present invention. A pulsating flow profile generated solely by the pump structure without any involvement of the herein described pressure release valve, as it is possible for it to occur already with the standard use of an infusion pump, may however occur even with a constant operation of the infusion pump.

In certain exemplary embodiments, the conveyance is achieved at a continuous flow rate, as long as the blood pump conveys with a continuous flow rate, or, always then when the blood pump conveys with a continuous flow rate.

In certain exemplary embodiments, conveying at a continuous flow rate continues until the flow rate of the infusion pump is manually or automatically changed. Subsequently, it may again be conveyed at a continuous second flow rate, wherein the first flow rate is different from the second flow rate.

The extracorporeal blood circuit may comprise in addition to the blood conducting main line one or several infusion lines, which are connected to a blood conducting line via Tees. Tees may be resin parts with three openings, which are connected via T-shaped fluid line. The fluid line may also be designed as y-shaped or similar. Tees may be glued in as inserts in a tubing system, through which the main line of the tubing system, e.g. the blood conducting line, may be connected to the infusion line.

Some or all embodiments may encompass one or several of the above or below mentioned advantages.

One advantage is that injecting the infusion solution in the blood—in contrast to continuously applying it, as this is known in the state of the art—leads to a short-termed swirling of the infusion solution within the blood, hence accelerating the mixing of the infusion solution with the blood.

One advantage of using the addition line or the blood circuit is that the described advantages may be achieved without having to carry out any changes on the controlling of the blood treatment apparatus or the pump for the infusion solution, because using the addition line causes no changes in the volume or in the concentration of the infusion solution supplied to the patient. The effect is achieved, with the known apparatuses, solely with the pulsating addition caused only by means of the on/off function of the pressure release valve. In particular, the infusion pump for the infusion solution conveys no differently than in the state of the art, i.e. preferably continuously. Its conveying manner may be maintained.

With this, it is advantageous that no constructive or other type of adaptation of the already delivered blood treatment apparatus, e.g. a software modification, is required. Implementation may be achieved by using the addition lines or blood tubing sets. A switch to the latter is therefore also easily achieved as it is anyhow a single-use article or a disposable.

The effect of the addition line is independent from the parameters of the blood treatment. If for example the flow rate of the blood pump is changed and in accordance therewith the flow rate of the pump for the infusion solution as well, there will be no change in how the addition line acts and effects. Alone the frequency at which the pressure release valve opens, may automatically adapt itself to the changed flow rate(s).

BRIEF DESCRIPTION OF THE DRAWINGS

Some embodiments shall be exemplary explained below with regard to the accompanying drawings in which identical reference numerals denote the same or similar components. The following applies in the partially highly simplified figures.

DETAILED DESCRIPTION OF THE DRAWINGS

Figure 1:
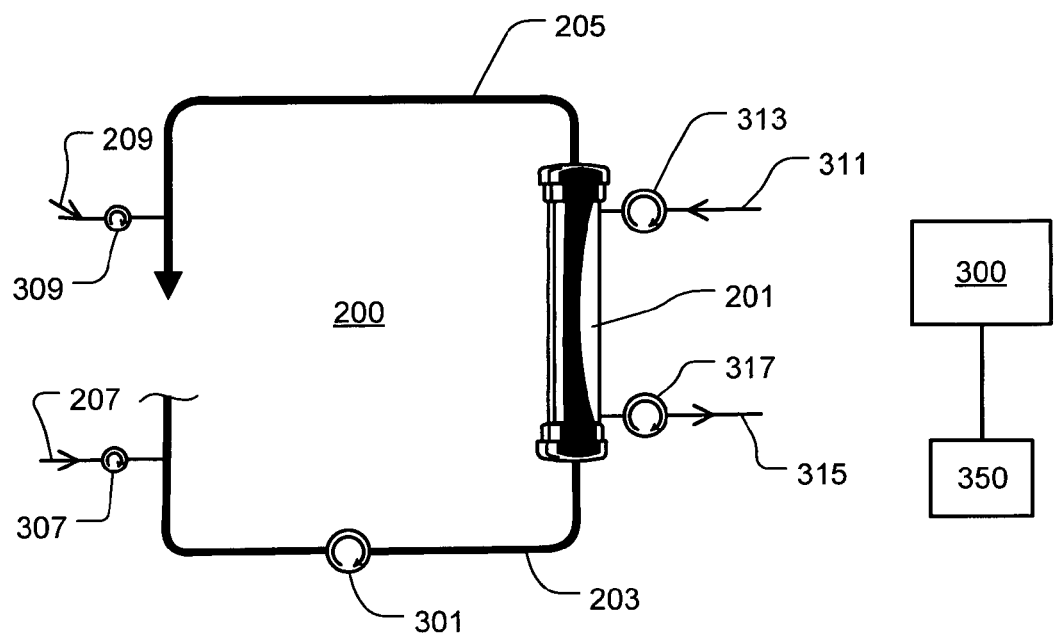
FIG. 1 shows the arrangement of an addition line at an extracorporeal blood tubing set.

FIG. 1 shows the basic arrangement of an addition line 209 at an extracorporeal blood tubing set 200, illustrated in a schematically highly simplified manner, in an exemplary embodiment of the blood tubing set.

The blood tubing set 200 comprises a hemofilter 201. A blood withdrawal line 203 (or arterial line) and a blood return line 205 (or venous line) are connected to the hemofilter 201, or dialyzer or blood filter.

The blood withdrawal line 203 is in an active communication with the blood pump 301 or comprises the latter.

A further addition line flows upstream of the blood pump 301, here a line 207 for citrate solution, into the blood withdrawal line 203.

The line 207 is in an active communication with, or comprises, a citrate pump 307.

The line 209 for calcium solution flows downstream of the hemofilter 201 into the blood return line 205.

The line 209 is in an active communication with, or comprises, a calcium pump 309. Said line is fed or supplied by a source for an infusion solution shown only in FIG. 1, herein exemplarily a calcium source 319. The source may be a bag or a bottle. Optionally, the infusion solution may be generated on-line; in this case, the respective device is considered as the source for generating.

The hemofilter 201 is connected to a line 311 for fresh dialysis fluid and to a line 315 for spent dialysate or filtrate. The line 311 is connected to, or comprises, a dialysis fluid pump 313. The line 315 is connected to, or comprises, a filter pump 317.

The shown arrow heads respectively indicate the flow direction when using the blood tubing set 200 as intended.

Figure 2:
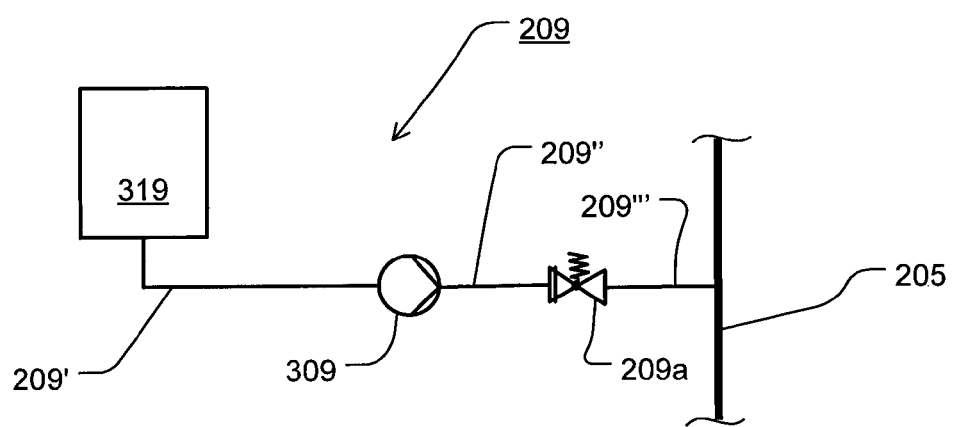
FIG. 2 shows details of the addition line of FIG. 1 with a pressure release valve.

The blood tubing system 200 shown in FIG. 1 may correspond to a known extracorporeal blood tubing set and be suitable particularly for the CVVHD (continuous venovenous hemodialysis), except for the line 209 for calcium shown in FIG. 2 as an example of an addition line for infusion solution.

The pumps 301, 307, 309, 313, and 317 may be part of an only schematically indicated blood treatment apparatus 300. The same applies for lines 311 and 315.

The blood treatment apparatus 300 may comprise, or be connected, to a control device 350.

The control device 350 may be designed and used for controlling or regulating. It can be a regulating device.

The control device 350 can be part of the blood treatment apparatus 300, it may be arranged externally to the blood treatment apparatus or separate thereof. The control device may be programmed to control or regulate the calcium pump 309—and optionally also further pumps, in particular those aforementioned—or other components of the blood treatment apparatus 300.

FIG. 2 shows, schematically highly simplified, details of the addition line or line 209 for calcium of FIG. 1 having a pressure release valve 309 in an exemplary embodiment of the line 209 or the addition line.

Line 209 extends between the source 319 for infusion solution, presently a calcium solution source, and a blood line, presently the blood return line 205, i.e. the venous patient line.

Thereby, the line 209 is in an active communication with the calcium pump 309 or comprises it, as explained with respect to FIG. 1.

The line 209 comprises, downstream of the calcium pump 309, which conveys towards the blood return line 209 during treatment, a pressure release valve 209a or is connected therewith. The pressure release valve 209a may be a known check valve.

With respect to the calcium pump 309 and the pressure release valve 209a, line 209 may be divided into section 209', which extends between the source 319 and the pump 309, section 209", which extends between the pump 309 and the pressure release valve 209a and section 209''', which extends between pressure release valve 209a and the connection to the blood return line 205.

The pressure release valve 209 allows a flow through only after a sufficiently high pressure upstream thereof has built up. With the pump 319 conveying continuously, a pulsating flow of infusion solution, which may flow into the blood line, is thus generated by (exclusively) the pressure release valve 209a.

It is advantageous if the coupling between pump 309 and pressure release valve 209a is damped. This may exemplarily be achieved in that the hose material of line 209 allows, at least in its section 209", i.e. between pump 309 and pressure release valve 209a, for an elastic deformation or is elastically deformable. Section 209" may therefore be designed as a flexible hose but preferably not as a metal tube. The elastic deformability allows to arrange an optional solution reservoir between pump 309 and pressure release valve 209a, wherein the reservoir may be able to receive the fluid volume conveyed by the pump 309 between closing of the pressure release valve 209a and a subsequent opening.

In addition, a drop of pressure (can be measured upstream of the pressure release valve 209a) to below the opening pressure of the pressure release valve 209) due to a pressure release valve 209a closing sufficiently slowly may take place. The valve closing sufficiently slowly may be intended in some embodiments.

A pressure release valve, closing sufficiently slowly, may be understood in some particular embodiments as a valve which—optionally in an interaction with a suitable hose, e.g. as described supra—allows a pulsating conveyance. A valve reacting rapidly to pressure changes such that a pressure, directly upstream of the valve, cannot drop to below the opening pressure, is not considered as sufficiently slow in the sense referred to herein. "Sufficiently slow" may be understood, however, as a pressure-compensation valve opening at an opening pressure and closing at a preselected or pre-selectable, and preferably constant, closing pressure, wherein the closing pressure is lower than the opening pressure "Sufficiently slow" may further be understood as a pressure-compensation valve opening at an opening pressure, at an initial point of time, and closing again first after the end of a preselected or sufficient period of time, at a later, second point of time. This may also enable the valve to close at a closing pressure being less than the opening pressure.

The size or volume of the aforementioned solution reservoir between the pump 309 and the pressure release valve 209a may exemplarily be determined by selecting a defined length of the section 209". 1 ml is reasonable.

The pump 309 may be designed as a roller pump, a piston pump, a centrifugal pump, a diaphragm pump or any other type. In particular, it may be peristaltic or occlusive. Preferably however, the pump 309 is a continuously conveying pump, employed to also convey continuously, i.e. with constant flow rate.

The flow rate may be set or preset or adjusted at 0.1 ml/min, 0.6 ml/min, 1.4 ml/min and at any other desired intermediate value.

Figure 3:
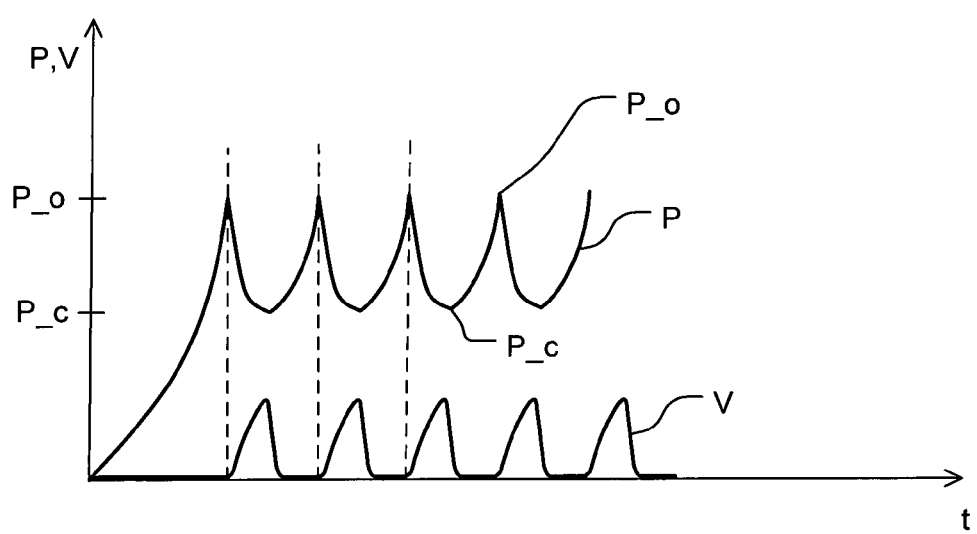
FIG. 3 shows the inlet pressure, which may prevail at the pressure release valve of FIG. 2, and the velocity corresponding respectively to the inlet pressure of an infusion solution when flowing in the addition line

FIG. 3 shows in one diagram both an inlet pressure p and a flow velocity v over time t.

The inlet pressure p is the pressure at the inlet of the pressure release valve 209a of FIG. 2, i.e. in particular in section 209" of line 209 at a point of time t.

The flow velocity v indicates the velocity of an infusion solution, corresponding respectively to the inlet pressure p, with which the solution flows through line 209 and in particular its section 209'''.

In the diagram of FIG. 3 the opening pressure p_o and the closing pressure p_c for the pressure release valve 209a are shown. The pressure required for the pressure release valve 209a to open is reached at the opening pressure p_o. The pressure release valve 209a is completely closed at the closing pressure p_c.

The courses or curves shown in FIG. 3 should be considered as idealized.

LIST OF REFERENCE NUMERALS

200 Blood tubing set
201 hemofilter or blood filter or dialyzer

203 Blood withdrawal line
205 Blood return line
207 Line for citrate solution
209 Line for calcium solution; addition line
209' Section
209" Section
209''' Section
209a Pressure release valve
300 Blood treatment apparatus
301 Blood pump
307 Citrate pump
309 Calcium pump
311 Line for dialysis fluid
313 Pump for dialysate
315 Line for dialysate, filtrate
317 Pump for dialysate, filtrate
319 Source of infusion solution, calcium source
350 Control or regulating device

The invention claimed is:

1. An extracorporeal blood circuit comprising:
at least one blood return line comprising at least one line section; and
at least one addition line for adding an infusion solution to a fluid flowing in the extracorporeal blood circuit, wherein the at least one addition line directly connects to the at least one line section of the blood return line, wherein the at least one addition line comprises:
a pressure release valve or a check valve arranged along the at least one addition line downstream of a rotary pump disposed along the at least one addition line and upstream of the at least one blood return line connected to the at least one addition line;
wherein the rotary pump is operable to continuously convey the infusion solution in the at least one addition line; and
wherein the pressure release valve or the check valve is configured to open to fluidly connect the at least one addition line to the at least one blood return line only when a fluid pressure upstream of the pressure release valve or the check valve reaches a predetermined threshold to produce a pulsating flow of the infusion solution into the at least one blood return line.

2. The extracorporeal blood circuit according to claim 1, wherein the at least one addition line is connected in fluid communication to the at least one blood return line.

3. The extracorporeal blood circuit according to claim 1, wherein the infusion solution is a calcium solution.

4. A blood treatment system comprising:
an extracorporeal blood circuit comprising
at least one blood return line comprising at least one line section; and
at least one addition line for adding an infusion solution to a fluid flowing in the extracorporeal blood circuit, the at least one addition line being directly connected to the at least one line section of the blood return line; and a blood treatment apparatus comprising:
a rotary infusion pump for conveying an infusion solution at a continuous flow rate within the at least one addition line and a blood pump for conveying blood within the at least one blood return line, wherein the rotary infusion pump is controlled by a control device,
wherein the at least one addition line comprises a pressure release valve or a check valve arranged along the at least one addition line downstream of the rotary infusion pump and upstream of the at least one blood return line; and
wherein the pressure release valve or the check valve is configured to open to fluidly connect the at least one addition line to the at least one blood return line only when a fluid pressure upstream of the pressure release valve or the check valve reaches a predetermined threshold to produce a pulsating flow of the infusion solution into the at least one blood return line.

5. The blood treatment system according to claim 4, wherein the control device is set or adapted or programmed to prompt the rotary infusion pump to convey continuously.

6. The blood treatment system according to claim 4, wherein the control device is not set or programmed to prompt the rotary infusion pump to convey in a pulsating manner.

7. A method of controlling a rotary infusion pump for conveying an infusion solution within an addition line, the method comprising:
providing an addition line for adding an infusion solution to a fluid flowing in an extracorporeal blood circuit, wherein the addition line is directly connected to a line section of a blood return line, wherein the addition line comprises a pressure release valve or a check valve;
connecting the rotary infusion pump to a source of the infusion solution;
connecting the rotary infusion pump to a pump section of the addition line; and
conveying the infusion solution by operating the rotary infusion pump with a continuous flow rate, wherein the pressure release valve or the check valve opens to fluidly connect the addition line to the blood return line only when a fluid pressure upstream of the pressure release valve or the check valve reaches a predetermined threshold to produce a pulsating flow of the infusion solution into the blood return line.

8. The method according to claim 7, wherein conveying at a continuous flow rate is achieved when or while or as long as a blood pump conveys at a continuous flow rate.

9. The method according to claim 7, wherein conveying at a continuous flow rate continues until a manual or an automatic change of the flow rate of the rotary infusion pump is carried out or taken.

10. The method according to claim 7, wherein conveying at a continuous flow rate is not a pulsating conveyance.

* * * * *